US006929627B2

(12) United States Patent
Mahoney

(10) Patent No.: US 6,929,627 B2
(45) Date of Patent: Aug. 16, 2005

(54) SUPPORT DEVICE FOR OSTOMY APPLIANCE

(76) Inventor: James L. Mahoney, 3600 Mary Anderson Rd., Wadesville, Posey County, IN (US) 47638

( * ) Notice: Subject to any disclaimer, the term of this patent is extended or adjusted under 35 U.S.C. 154(b) by 167 days.

(21) Appl. No.: 10/426,508

(22) Filed: Apr. 30, 2003

(65) Prior Publication Data

US 2003/0204175 A1 Oct. 30, 2003

Related U.S. Application Data

(60) Provisional application No. 60/376,313, filed on Apr. 30, 2002.

(51) Int. Cl.[7] .............................. A61F 5/44; A61F 11/00
(52) U.S. Cl. ....................................... 604/332; 606/108
(58) Field of Search ................................. 604/277, 327, 604/332–345, 355; 606/108; 600/32

(56) References Cited

U.S. PATENT DOCUMENTS

| | | | | |
|---|---|---|---|---|
| 4,187,850 A | * | 2/1980 | Gust ........................... | 604/338 |
| 4,205,678 A | * | 6/1980 | Adair ......................... | 604/343 |
| 4,344,433 A | * | 8/1982 | Smith ......................... | 604/344 |
| 4,517,972 A | * | 5/1985 | Finch, Jr. ...................... | 602/2 |
| 4,726,354 A | * | 2/1988 | Fujita ........................... | 600/32 |
| 6,027,510 A | * | 2/2000 | Alt .............................. | 606/108 |
| 6,328,720 B1 | * | 12/2001 | McNally et al. ............. | 604/332 |
| 6,409,709 B1 | * | 6/2002 | Recto .......................... | 604/339 |
| 6,840,924 B2 | * | 1/2005 | Buglino et al. ............. | 604/337 |
| 2003/0040727 A1 | * | 2/2003 | Boulanger et al. .......... | 604/332 |
| 2004/0106908 A1 | * | 6/2004 | Leise et al. ................. | 604/332 |

FOREIGN PATENT DOCUMENTS

| | | | | |
|---|---|---|---|---|
| GB | 2 119 654 A | * | 11/1983 | ............. A61F/5/44 |
| WO | WO 88/03035 | * | 5/1988 | .......... A61M/25/00 |

* cited by examiner

*Primary Examiner*—Larry I. Schwartz
*Assistant Examiner*—Michael G. Bogart
(74) *Attorney, Agent, or Firm*—Gary K. Price, Esq.

(57) ABSTRACT

A support device used when applying an ostomy appliance to a wearer, and in particular, a device that assists the wearer in applying the body side member of the ostomy appliance without substantial use of the wearer's arms or hands. The support device assists the wearer to apply steady pressure to the body side member until proper sealing is obtained between the body side member and wearer's skin. The preferred embodiment includes a base member sized to releasably accept the body side member, the base member including an opening sized to the approximate circumference of a stoma opening of the body side member. The support device further includes an end member, and first and second support members vertically disposed between the base member and the end member.

9 Claims, 3 Drawing Sheets

SUPPORT DEVICE FOR OSTOMY APPLIANCE

CROSS REFERENCES TO RELATED APPLICATIONS

U.S. Provisional Application for Patent 60/376,313, filed Apr. 30, 2002, with title "Support Device for Ostomy Appliance" which is hereby incorporated by reference. Applicant claims priority pursuant to 35 U.S.C. par. 119(e) (I).

STATEMENT AS TO RIGHTS TO INVENTIONS MADE UNDER FEDERALLY SPONSORED RESEARCH AND DEVELOPMENT

Not Applicable

BACKGROUND OF THE INVENTION

1. Field of the Invention

This invention relates to a support device used when attaching an ostomy appliance, and in particular a device to assist in attaching the appliance's adhesive body side member to the skin of the wearer's abdomen. The present invention further relates to a method of applying the body side member to the wearer's abdomen.

2. Brief Description of Prior Art

As part of treatment for some types of cancer, including colon cancer or rectum cancer, as well as other diseases, it is often medically necessary for a patient to undergo an enterostomy. This involves making an opening in the intestine through the abdominal wall. An ostomy appliance is then connected to the opening to receive fecal material from the intestine.

Ostomy appliances are well known in the art, and generally includes a body side member that is adhesively attached to the wearer's abdomen, and a receiving member or bag attached to the body side member for receiving waste products of the body. The body side member is usually adhered to the wearer's skin by means of an adhesive wafer having an inlet opening for accomodating a stoma.

The service time of the body side member is dependant upon factors including the amount and aggressiveness of the exudates, and the adhesive seal between the member and the wearer's abdomen. Frequent changing of the body side member is undesirable due to the irritation of the skin. Further, the quality of life may be improved and the nuisance of wearing an ostomy appliance may be reduced if the intervals between exchanging of the body side member can be increased.

When adhesively applying the body side member to the skin of the wearer's abdomen, it is known to position the adhesive wafer portion of the body side member over the appropriate abdomen area and manually apply the member to the skin. It is further known that the member must be manually held in place until the adhesive is sufficiently tacky to secure the body side member in place and sufficiently seal the member to the skin of the wearer's abdomen. Again, if not sufficiently sealed, the body member will need replacing more frequently.

The inventor has found that when applying the body side member to the wearer's skin as discussed above, it takes at least three (3) minutes for the member to sufficiently seal to the wearer's skin. As such, the wearer is required to manually apply steady pressure to the member until such sealing is obtained. Such consistent application of pressure by the wearer would be difficult, if not impossible for the wearer when the wearer for example, suffers from arthritis in the joints of the hands or arms, or has some other debilitating disease that generally prohibits or limits the use of arms or hands.

The inventor is unaware of a device that assists the wearer in sufficiently applying the body side member without substantial use of the wearer's arms or hands, and in particular, a device that will apply steady pressure to the body side member until proper sealing is obtained between the body side member and wearer's skin.

As will be seen from the subsequent description, the preferred embodiments of the present invention overcome these and other shortcomings of prior art.

SUMMARY OF THE INVENTION

This invention relates to the field of ostomy devices, to a support device used when attaching an ostomy appliance, and in particular a device that assists the wearer in sufficiently applying the body side member of the ostomy applicance without substantial use of the wearer's arms or hands. The device of the present invention will apply steady pressure to the body side member until proper sealing between the body side member and the wearer's skin is obtained. The preferred embodiment includes a base member sized to releasably accept the body side member, the base member including an opening sized to the approximate circumference of a stoma opening of the body side member. The support device further includes an end member, and first and second support members vertically disposed between the base member and the end member.

DESCRIPTION OF THE PREFERRED EMBODIMENT

In accordance with the present invention, a support device of ostomy appliance is used to assist the wearer in attaching the ostomy appliance's adhesive body side member to the skin of the wear's abdomen. Specifically, the support device of the present invention applies steady pressure to the body side member until proper sealing is obtained between the member and the wear's skin without substantial use of the wear's arms or hands. In the broadest context, the support device for ostomy appliance consists of components figured and collated with respect to each other so as to attain the desired objective.

Figure 1:
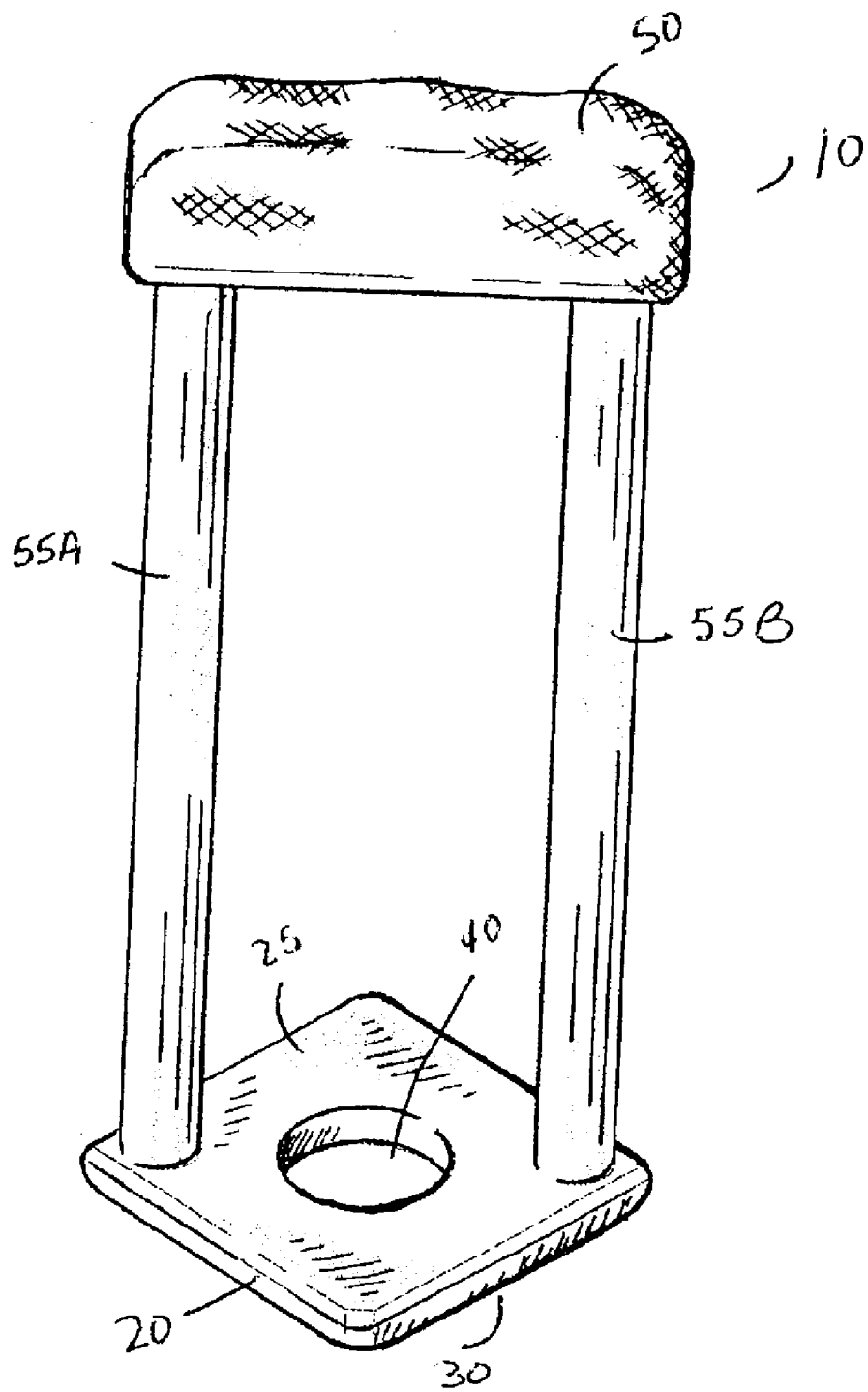
FIG. 1 is a perspective view of the components of a preferred embodiment of the present invention, namely, a base member, an end member, and first and second support members.
Figure 2:
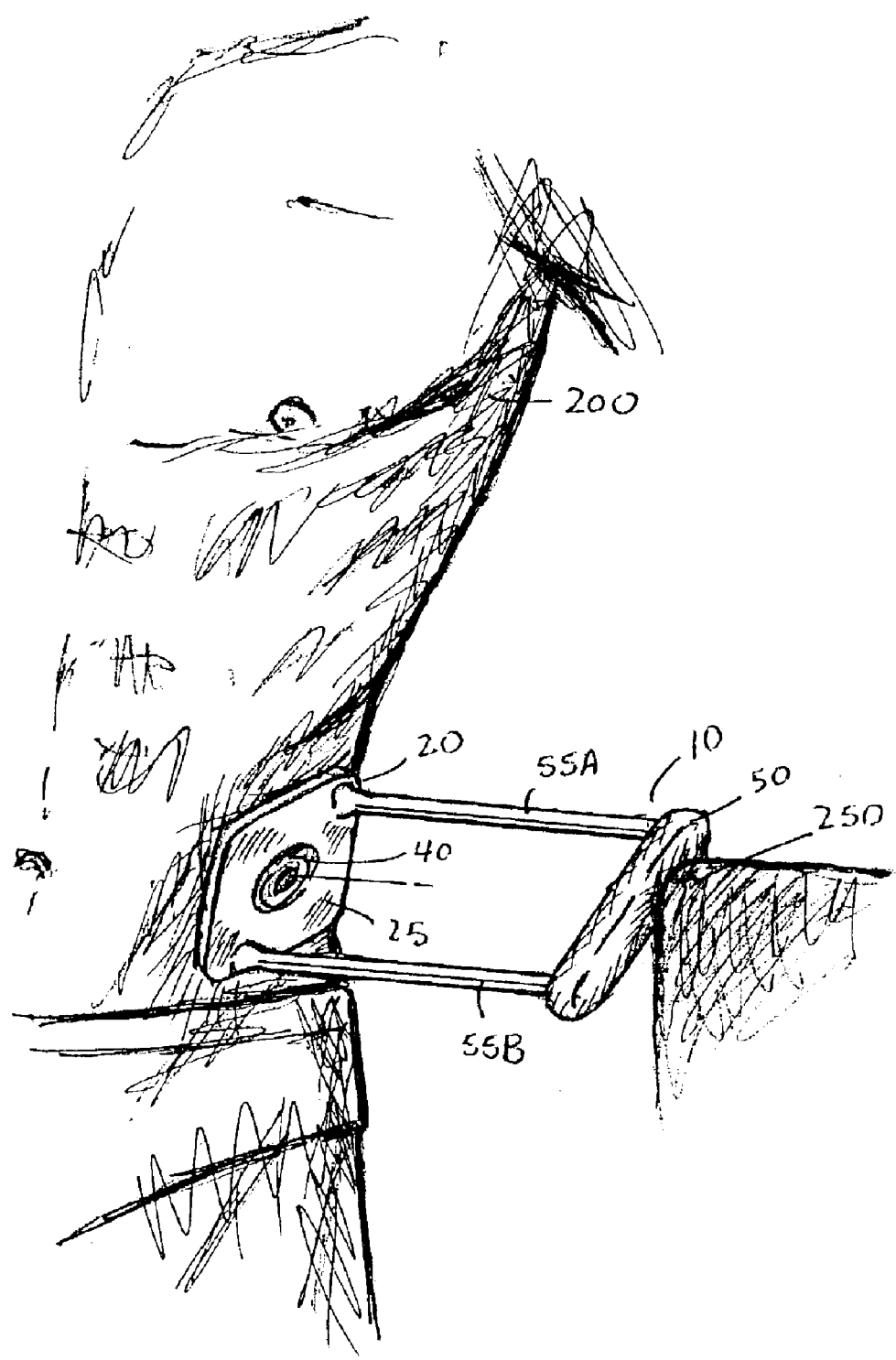
FIG. 2 is a perspective view of the device of FIG. 1 applying the body side member of the ostomy appliance to the skin of the wearer's abdomen.
Figure 3:
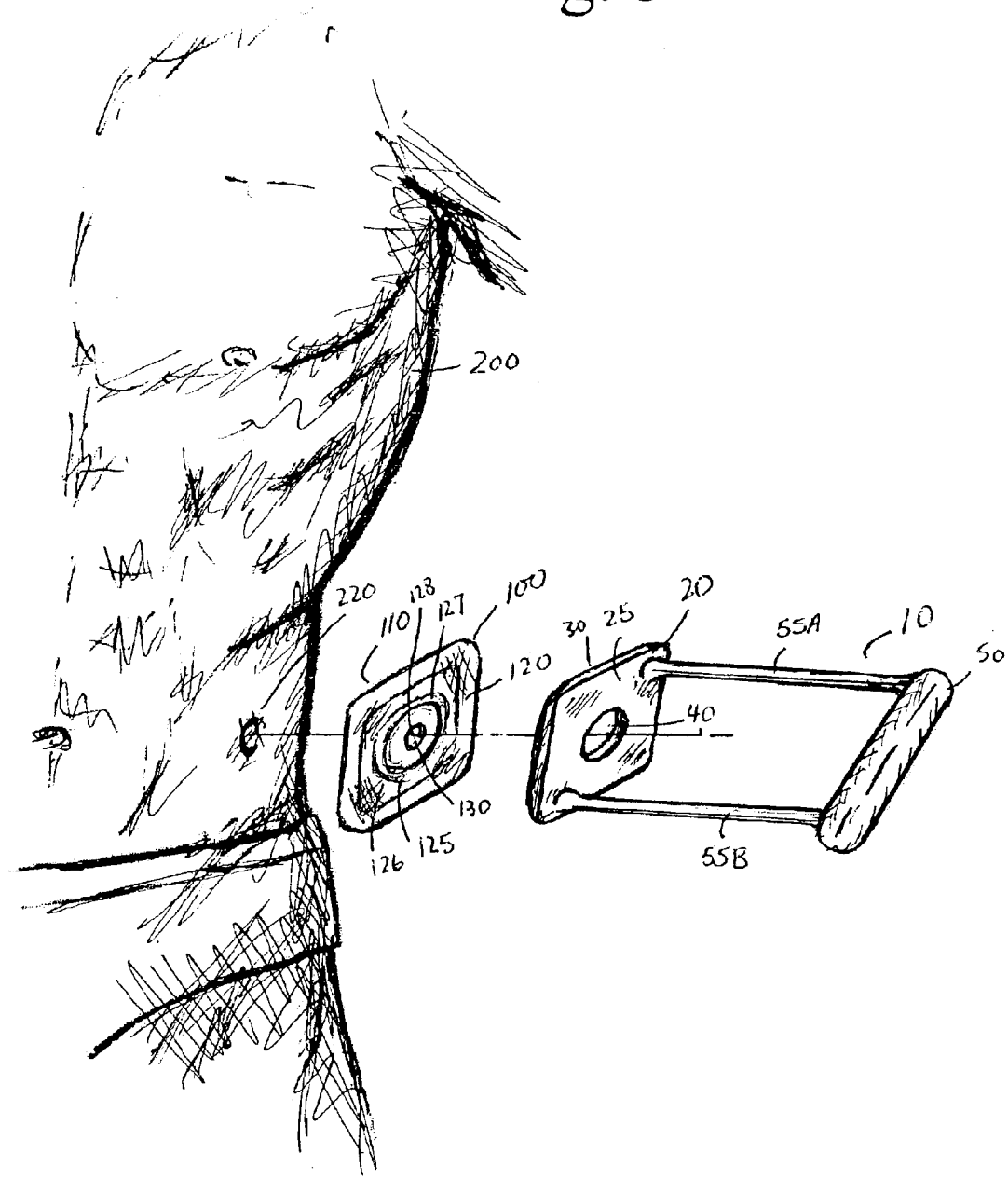
FIG. 3 is an exploded perspective view of the device of FIG. 1 applying the body side member of the ostomy appliance to the skin of the wearer's abdomen.

FIGS. 1–3 illustrate a preferred embodiment of a support device 10 for an ostomy appliance made in accordance with the present invention. Said support device 10 generally having a base member 20, an end member 50, and first and second support members 55A and 55B. The support device 10 having a base member 20 sized to releasably accept a prior art body side member 100 of an ostomy appliance.

As shown in FIG. 3, a typical body side member 100 includes a back side 110, the back side 110 having a substantially flat surface and including an adhesive skin barrier portion (not shown) conventionally used. The body side member 100 further including a front side 120, the front side 120 having a prior art wafer 125 attached in the approximate center of the front side 120, and a stoma opening 130 disposed in the center of the member 100. The wafer 125 includes portions that extend from the front side 120 namely a first edge 126, and a ring 127. The wafer 125 further including a wafer opening 128 disposed in the approximate center of the wafer 125 and in alignment with the stoma opening 130 of the body side member 100. The body side member 100 generally having a substantially rectangular configuration.

The base member 20 having a first side 25, a second side 30 and an opening 40, the opening 40 disposed in the center of the base member 20 and sized to the approximate circumference of the stoma opening 130 of the body side member 100. The second side 30 sized and configured to releasably receive the front side 120 of the body side member 100. In the preferred embodiment, the second side 30 includes a first indention (not shown) sized to receive the first edge 126 of the wafer 125, and a second indention (not shown) to receive the ring 127 of the wafer 125.

As should be appreciated from the description herein, the base member 20 is symmetrically constructed so that the second side 30 is preferably identical to receive the front side 120 of the body side member 100, with the exception that the second side 30 of the base member 20 has the first and second indentions described above to receive the extended portions 126, 127 of the wafer 125 of the front side 120 of the body side member 100.

One end of the support members 55A and 55B attach to the first side 25 of the base member 20, and the opposite ends of the support members 55A and 55B are attached to the end member 50, so that the support members 55A and 55B are vertically disposed between the base member 20 and the end member 50. In application, as shown in the drawings, the first support member 55A is parallel to the second support member 55B.

As discussed, the support device 10 is used when attaching the ostomy appliance, and in particular assists a wearer 200 in applying the body side member 100 of the ostomy applicance to the wearer's 200 abdomen without substantial use of the wearer's 200 arms or hands.

The device 10, and the methods described herein, will apply steady pressure to the body side member 100 until proper sealing is achieved between the adhesive skin barrier portion of the back side 110 of the member 100 and the wearer's 200 skin.

In use, the wearer 200 positions the body member 100 over a stoma 220 of the wearer's 200 abdomen. The wearer 200 then adhesively attaches the back side 110 of the body member 100 to the skin of the wearer's 200 abdomen so that the stoma 220 is in alignment with the stoma opening 130 of the body member 100. Once in position, the wearer 200 must apply steady pressure to the body member 100 against the wearer's 200 skin until proper sealing between the body side member 100 and the wearer's 200 skin is achieved. This is done, as shown in FIG. 3, by positioning the support device 10 over the front side 120 of the body member 100 so that the second side 30 of the base member 20 receives the front side 120 of the body member 100 as previously described. As shown in FIG. 2, with the base member 20 attached to the body member 100, the wearer 200 props the end member 50 to a table corner 250, or the like, and slightly leans towards the table corner 250 so that the support device 10 remains positioned on the body member 100. It should be obvious that slightly leaning towards the table corner 250 as discussed above holds the body member 100 in place and will cause a consistent and continuous application of pressure to the body side member 100 while it is sealing to the skin of the wearer's 200 abdomen. It should be further obvious that such pressure is achieved without substantial use of the wearer's hands or arms. Once the member 100 is sufficiently sealed to the wearer's 200 abdomen, the wearer removes the support device 10 from the body side member 100.

Although the description above contains many specificities, these should not be construed as limiting the scope of the invention but as merely providing illustrations of a presently preferred embodiment of this invention.

Thus the scope of the invention should be determined by the appended claims in the formal application and their legal equivalents, rather than by the examples given.

I claim:

1. A support device used to apply a body side member of an ostomy appliance to the skin of a wearer's abdomen, said support device comprising:

a base having an opening sized and configured to releasably receive the body side member, an end member, and at least one support member disposed between the base and the end member, a side, including a first indention sized to receive a first edge of a wafer attached to the body side member, said side further including a second indention sized to receive a ring of the wafer.

2. The support device as recited in claim 1, wherein the opening in the base is sized to the approximate diameter of a stoma opening of the body side member.

3. The support device as recited in claim 1, wherein the at least one support member is vertically disposed between the base and the end member.

4. A support device used to apply a body side member of an ostomy appliance to the skin of a wearer's abdomen, said body side member having a back side with an adhesive skin barrier, and a front side having a wafer attached in the approximate center of the front side, and a stoma opening, said support device comprising:

a base member having a first side, a second side, and an opening disposed in the center of the base member, wherein the second side of the base member including a first indention sized to receive a first edge of the wafer, said second side sized and configured to releasably receive the front side of the body side member, an end member, and a first and second support members having one end attached to the first side of the base member, and the opposite end attached to the end member, so that said first and second support members are vertically disposed between the base member and the end member.

5. The support device as recited in claim 4, wherein the first support member is in parallel relationship with the second support member.

6. A method for applying pressure to a body side member of an ostomy appliance until proper sealing is obtained between the body side member and skin of a wearer's abdomen, the method comprising:

providing a support device having a base sized and configured to releasably receive the body side member, said base having an opening sized and configured to releasably receive the body side member, said support device further including an end member and at least one support member, wherein one end of the support member is attached to the base and the opposite end of the support member is attached to the end member, positioning the base to receive the body side member, applying pressure to the body side member by supporting the end member to a structure, leaning slightly towards the structure to apply pressure to the body side member until the body side member has sufficiently sealed to the skin of the wearer's abdomen, and removing the support device from the body side member.

7. The method as recited in claim 6, wherein the opening in the base is sized to the approximate diameter of a stoma opening of the body side member.

8. The method as recited in claim 6, wherein the support device further including a side, said side having a first indention sized to receive a first edge of a wafer attached to the body side member and a second indention sized to receive a ring of the wafer.

9. The method as recited in claim 6, wherein the at least one support member is vertically disposed between the base and the end member.

* * * * *